Figure 1:
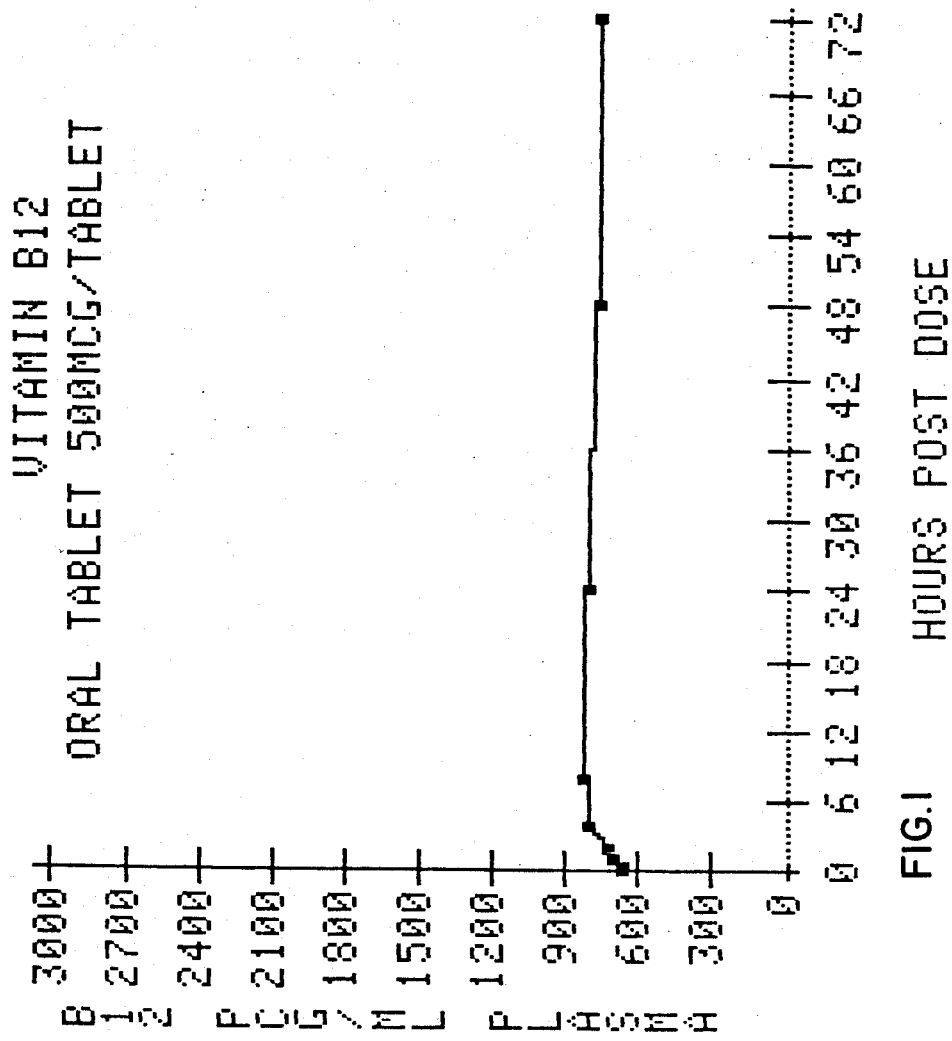

United States Patent [19]

Wenig

[11] Patent Number: 4,724,231

[45] Date of Patent: Feb. 9, 1988

[54] NASEL COMPOSITIONS CONTAINING VITAMIN $B_{12}$

[75] Inventor: Jeffrey Wenig, Dix Hills, N.Y.

[73] Assignee: Nastech Pharmaceutical, Inc., Hauppauge, N.Y.

[21] Appl. No.: 848,690

[22] Filed: Apr. 8, 1986

Related U.S. Application Data

[63] Continuation-in-part of Ser. No. 723,844, Apr. 16, 1985, abandoned.

[51] Int. Cl.$^4$ .............................................. A61K 31/70
[52] U.S. Cl. ..................................................... 514/52
[58] Field of Search ............................ 514/52; 424/45

[56] References Cited

U.S. PATENT DOCUMENTS 4,174,295 11/1979 Bargigia et al. ...................... 424/45
4,525,341 6/1985 Deihl .................................... 514/52

OTHER PUBLICATIONS

Chem. Abst. 66: 64246e (1967)–Shinton et al.
Chem. Abst. 77: 105,623y (1972)–Forest Laboratories.

*Primary Examiner*—Douglas W. Robinson
*Attorney, Agent, or Firm*—Wyatt, Gerber, Shoup, Scobey and Badie

[57] ABSTRACT

This invention is directed to compositions for nasal administration of a vitamin $B_{12}$ to a human suffering a vitamin $B_{12}$ deficiency. It is also directed to such compositions in dosage unit form and with methods of administering such compositions.

27 Claims, 4 Drawing Figures

NASEL COMPOSITIONS CONTAINING VITAMIN $B_{12}$

BACKGROUND OF THE INVENTION

Cyanocobalamin is a vitamin $B_{12}$, and is one of the $B_{12}$ class of vitamins which icnludes vitamin $B_{12a}$ (hydroxocobalamin), vitamin $B_{12b}$ (aquacobalamin), vitamin $B_{12c}$ (nitrilocobalamin), coenzyme $B_{12}$ (5'Odeoxyadenosine cobalamine) and methyl $B_{12}$ (methyl cobalamine). Cyanocobalamin is the principal member of the class, and the most widely employed in medicine. This invention will be described as it relates to cyanocobalamin, but those skilled in the art will recognize that the invention is aplicable to the class.

Vitamin $B_{12}$ is an essential compound for normal growth, hematopoiesis, production of all epithelial cells and maintenance of myelin throughout the nervous system. It was first isolated from liver concentrate by Rickes and his coworkers in 1948 and structural elucidated by Hodgkin and her coworkers in the late 1950's. It is currently commercially available as a tablet and as an injectable.

Therapeutically, vitamin $B_{12}$ is employed in the treatment of a variety of $B_{12}$ deficiency afflictions, principally anemias such as pernicious and diplyllobothrium latum. Although the minimum daily requirement of vitamin $B_{12}$ is approximately 0.1 $\mu g$, the generally prescribed initial therapeutic dose is 100 to 1000 $\mu g$ given intramuscularly. Maintenance therapy with vitamin $B_{12}$ is usually 100 $\mu g$ intramuscularly, monthly and must be continued for life.

Since pernicious anemia is often a disease of later years when many sufferers have reduced muscle mass or are atrophic, repeated intramuscular injections of vitamin $B_{12}$ can be inconvenient, painful and often require doctor's visits. In some cases at least in the early stages, hospitalization is required. As a result, there is a need for a more convenient, less painful and less expensive method of administering vitamin $B_{12}$, particularly one that would not require hospitalization or repeated physician contacts.

Unfortunately, up to the present time no efficient method of administering $B_{12}$ which will achieve therapeutically useful blood levels of the vitamin except parenteral administration has been devised.

In 1953 and 1954 Monto et al in Am. J. Med. Sci., 223, 113 (1953) and Arch. of Int. Med. 93,219 (1954) described administration of $B_{12}$ by nasal inhalation and instillation. The vehicles for administration were aqueous isotonic sodium chloride solution and lactose powder. Although the results were reported as effective, safe and economical, the fact is that parenteral administration remains the only method regarded by the medical community as a safe, reliable and effective method for treating vitamin $B_{12}$ deficiencies in humans. No composition for nasal inhalation or instillation has become commercially available for nasal administration to mammals. Neither have there been any further publications describing nasal inhalation or instillation of which applicant is aware.

The difficulty with nasal instillation by nasal dosage as the procedure is described in the cited articles is that most of the $B_{12}$ passes immediately into the throat. It is not in contact with the nasal mucosa for a sufficient period of time to permit useful and uniform absorption. Most of the $B_{12}$ so administered is, in fact wasted.

Compositions have now been discovered for the nasal administration of $B_{12}$ which can be kept in contact with the nasal mucosa for an extended period of time. During the time the compositions are in such contact, the $B_{12}$ is uniformly absorbed from the compositions through the nasal mucosa and is then uniformly distributed systemically. The use of the compositions, because of the efficiency with which the $B_{12}$ is absorbed allows the use much lesser amounts of $B_{12}$ than is normally present in parenteral $B_{12}$ compositions. Moreover, since the patient can self administer the $B_{12}$, the need for hospitalization or physician contacts is minimized and may even be eliminated.

THE INVENTION

This invention provides vitamin $B_{12}$ containing compositions specifically formulated for nasal administration which will, unlike aqueous isotonic sodium chloride compositions, remain in contact with the nasal mucosa for a sufficiently long period of time to permit consistent, continuous and uniform absorption of therapeutically effective amounts of a vitamin $B_{12}$ through the nasal mucous membrane.

The invention, therefore comprises compositions containing a therapeutically effective amount of a vitamin $B_{12}$, such compositions being sufficiently viscous to maintain themselves in the nasal passages for a period of time which is long enough so that most of the $B_{12}$ is absorbed. The compositions are stable, easy to handle, and may be self administered by the patient.

More specifically the compositions of the invention are for nasal administration and contain a therapeutically effective amount of a vitamin $B_{12}$ in an isotonic aqueous buffer at a pH of from about 4 to 6. The compositions may be in the form of gels, lotions, ointments, creams and the like and will contain a sufficient amount of a thickening agent so that the viscosity is from about 2500 to 6500 cps, although more viscous compositions even up to 10,000 cps may be employed. The preferred compositions have a viscosity of 2500 to 5000 cps, since above that range they become more difficult to administer.

Due to the efficiency with which the $B_{12}$ is adsorbed from the compositions of this invention, a therapeutically effective amount of $B_{12}$ for nasal administration will normally be appreciably less than for other methods of administration. Typically the concentration of $B_{12}$ in a composition of the invention will be 0.05% to 1% by weight based on the total weight. In dosage unit forms the dosage will normally be from about 50 to 1000 micrograms.

The pH of the compositions of this invention is from about 4 to 6. At this pH, $B_{12}$ is stable so that the compositions have a shelf life which may be a year or more. Additionally, at this pH, irritation of the nasal mucosa is minimal. The pH is maintained with a physiologically acceptable buffer composition suitably an acetate, citrate, phosphate, phthalate, borate, or other buffer.

Acetate and citrate buffers are preferred for convenience and economy.

The isotonicity of the composition is accomplished using sodium chloride, or other pharmaceutically acceptable agent such as dextrose, boric acid, sodium tartrate or other inorganic or organic solute. Sodium chloride is preferred particularly for buffers containing sodium ions.

Viscosity of the compositions is maintained at the selected level using a therapeutically acceptable thickening agent. Methyl cellulose is preferred because it is easily and economically available and is easy to work with. Other suitable thickening agents include, for example, xanthan gum, carboxymethyl cellulose, hydroxypropyl cellulose, carbomer, and the like. The preferred concentration of the thickener will depend upon the agent selected. The important point is to use an amount which will achieve the selected viscosity.

Preferred compositions within the scope of this invention will contain a humectant to inhibit drying of the mucous membrane and to prevent irritation. Any of a variety of humectants can be employed including, for example sorbitol, propylene glycol or glycerol. As with the thickeners, the concentration will vary with the selected agent, although the presence or absence of these agents, or their concentration is not an essential feature of the invention.

An enhanced absorption of $B_{12}$ across the mucous membrane can be accomplished employing a surfactant. Typically useful surfactants for these therapeutic compositions include polyoxyethylene derivatives of fatty acid partial esters of sorbitol anhydrides such as Tween 80, Polyoxyl 40 Stearate, Polyoxyethylene 50 Stearate and Octoxynol. The usual concentration is from 1% to 10% based on the total weight.

A preservative is generally employed to increase the shelf life of the compositions. Benzyl alcohol is suitable, although a variety of preservatives including, for example, Parabens, thimerosal, chlorobutanol, or benzalkonium chloride may also be employed. A suitable concentration of the preservative will be from 0.02% to 2% based on the total weight, although there may be appreciable variation depending upon the agent selected.

The therapeutically effective compositions of this invention are prepared by mixing the ingredients following generally accepted procedures. For example, the selected components may be simply mixed in a blender, or other standard machine to produce a concentrated mixture which is then adjusted to the final concentration and viscosity by the addition of water.

A typical composition of this invention contains the following components per 100 ml.

Benzyl alcohol, NF: 1.50 ml
Sodium chloride, NSP: 0.82 gm
Methyl cellulose, USP (400 cps): 2.00 gm
Acetic acid, NF: 0.10 gm
Sodium acetate (anhyd, USP): 0.27 gm
Sorbitol soln., USP: 5.00 ml
Cyanocobalamine, USP: 0.10 gm
Water, purified: q.s. 100.00 ml The viscosity of the formulation is about 4500 cps. The pH is about 5.

The following non-limiting examples are given by way of illustration only and are not to be considered limitations of this invention of which many apparent variations are possible without departing from the spirit or scope thereof.

EXAMPLE 1

The following compositions prepared by mixing.

A

Phenylmercuric Acetate NF: 0.002 g
Boric Acid NF: 1.740 g
Methylcellulose (4000 CPS) USP: 2.000 g
Acetic Acid NF: 0.100 g
Sodium Acetate (Anhydrous) USP: 0.270 g
Glycerin USP: 5.000 ml
Cyanocobalamin USP: 0.100 g
Water, Purified USP: q.s. 100.000 ml

B

Benzalkonium Chloride NF: 0.020 g
Potassium Chloride USP: 1.080 g
Hydroxyethyl Cellulose (3500–4000 CPS) NF: 1.000 g
Acetic Acid NF: 0.100 g
Sodium Acetate (Anhydrous) USQ: 0.270 g
Propylene Glocol USP: 5.000 ml
Cyanocobalamin USP: 1.000 g
Water, Purified USP: q.s. 100.000 ml

C

Thimerosal USP: 0.002 g
Dextrose USP: 5.120 g
Polysorbate 80 USP: 10.000 g
Methylcellulose (4000 CPS) USP: 1.33 g
Acetic Acid NF: 0.100 g
Sodium Acetate (Anhydrous) USP: 0.270 g
Glycerin USP: 5.000 ml
Cyanocobalamin USP: 0.500 ml
Water, Purified: q.s. 100.000 ml

D

Methylparaben NF: 0.020 g
Propylparaben NF: 0.010 g
Sodium Chloride USP: 0.820 g
Xanthan Gum NF: 2.000 g
Acetic Acid NF: 0.100 g
Sodium Acetate (Anhydrous) USP: 0.270 g
Propylene Glycol USP: 5.000 g
Cyanocobalamin USP: 0.200 g
Water, Purified: q.s. 100.000 ml The viscosities of the compositions are within the range defined above.

The typical composition disclosed above just prior to the examples was tested in humans in order to determine quantitative increases in $B_{12}$ Blood Levels following nasal administration. Three normal volunteers received 0.1 cc of the cited composition (100 μg $B_{12}$) inserted nasally with a nasal syringe applicator. Serial Blood Samples were drawn from the subjects at 0, 0.05, 0.08, 0.16, 0.25, 0.5, 1.0, 2.0, 3.0, 4.0, 6.0, 8.0, and 24 hours following dosing and assayed for $B_{12}$ content by radioimmunoassay.

It was found that in less than 15 minutes after administration the serum level of $B_{12}$ was significantly elevated and that significantly elevated blood levels were maintained during the full 24 hours of the study period.

The actual plasma blood levels of $B_{12}$, in the subjects following its nasal administration in the above cited composition, were:

| TIME (hours) | PLASMA LEVELS (Picograms) |
| --- | --- |
| 0 | 599 |
| 0.05 | 631 |
| 0.08 | 628 |
| 0.16 | 674 |
| 0.25 | 754 |
| 0.5 | 729 |
| 1.0 | 804 |
| 2.0 | 794 |
| 3.0 | 769 |
| 4.0 | 727 |
| 6.0 | 752 |
| 8.0 | 803 |
| 24.0 | 729 |

An additional and similar study was performed with three human subjects using the same composition in which 0.2 cc was administered intranasally (200 μg B12). The actual plasma blood levels obtained were:

| TIME (hours) | PLASMA LEVELS (Picograms) |
|---|---|
| 0.0 | 591 |
| 0.05 | 630 |
| 0.08 | 637 |
| 0.16 | 680 |
| 0.25 | 699 |
| 0.5 | 742 |
| 1.0 | 809 |
| 2.0 | 849 |
| 3.0 | 786 |
| 4.0 | 764 |
| 6.0 | 722 |
| 8.0 | 742 |
| 24.0 | 675 |

EXAMPLE 2

A composition of this invention containing the following components per 100 ml was prepared.
Benzyl Alcohol NF: 1.50 ml
Sodium Chloride USP: 0.82 g
Methyl Cellulose (400 cps.): 133. g
Acetic Acid NF: 0.10 g
Sodium Acetate (Anhydrous): 0.27 g
Sorbitol Solution USP: 5.00 ml
Cyanocoabalamin USP: 0.10 g
Water, Purified USP: q.s. 100.000 ml This composition was tested in three humans as described in the previous example. The nasal administration of 200 μg of $B_{12}$ in 0.2 cc gave the following serum $B_{12}$ levels:

| TIME (hours) | PLASMA LEVELS (Picograms) |
|---|---|
| 0.0 | 731 |
| 0.05 | 734 |
| 0.08 | 725 |
| 0.16 | 845 |
| 0.25 | 837 |
| 0.5 | 940 |
| 1.0 | 975 |
| 2.0 | 1027 |
| 3.0 | 1038 |
| 4.0 | 1002 |
| 6.0 | 969 |
| 8.0 | 945 |
| 24.0 | 925 |

Again it was found that in approximately 15 minutes after administration the serum level of $B_{12}$ was significantly elevated and that significantly elevated blood levels were maintained during the full 24 hours of the study period.

EXAMPLE 3

The following comparative experiment was conducted on forty normal, human, adult volunteers to compare the availability, speed of availability, and duration of availability of $B_{12}$ administered by various routes. Commercially available oral and sublingual tablets were compared with the compositions of this invention which were administered orally. All samples were tested by high performance liquid chromatography for $B_{12}$ per dosage unit was as follows:
Methyl Cellulose: 20 gm
Sodium Citrate: 3.2 gm
Citric Acid: 1.2 gm
Benzalkonium chloride 50%: 0.4 ml
Cyanocolalamine: 2.5 gm
Purified Water q.s. to: 100 ml The composition used to prepare the 400 mcg intranasal dosage unit was identical except that it contained 4.0 gm. of cyanocolalamine.

Serial blood samples were from the subjects at 0, 5, 1, 2, 4, 8, 24, 48 and 72 hours following dosing and assayed for $B_{12}$ content by radioimmunoassay.

Figure 2:
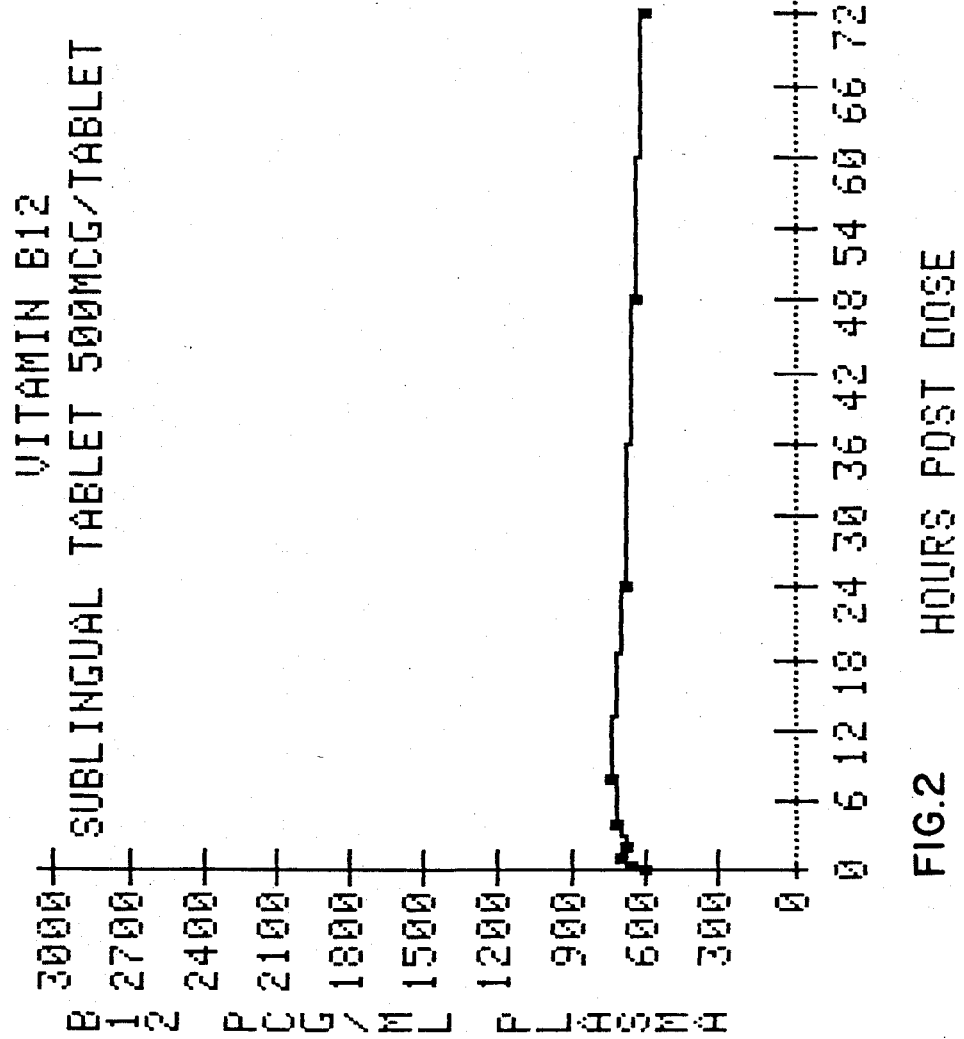
Figure 3:
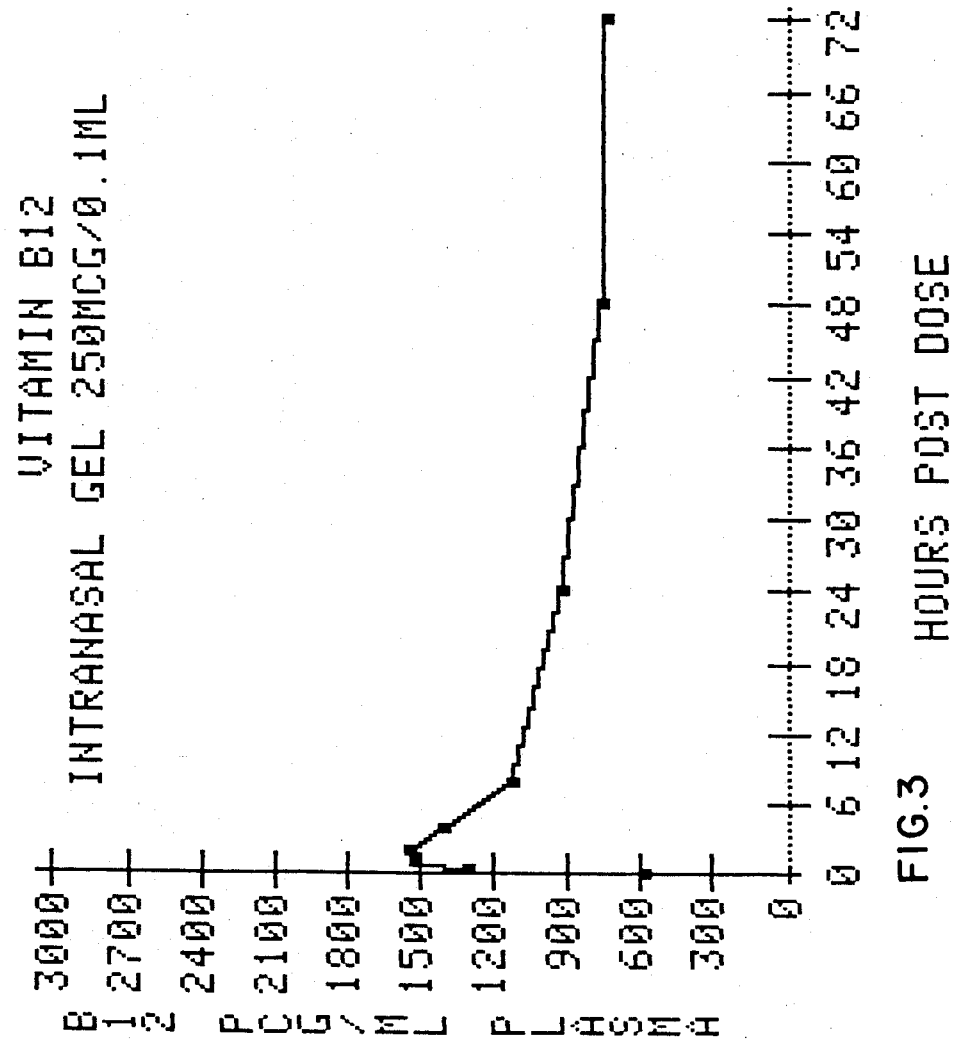
Figure 4:
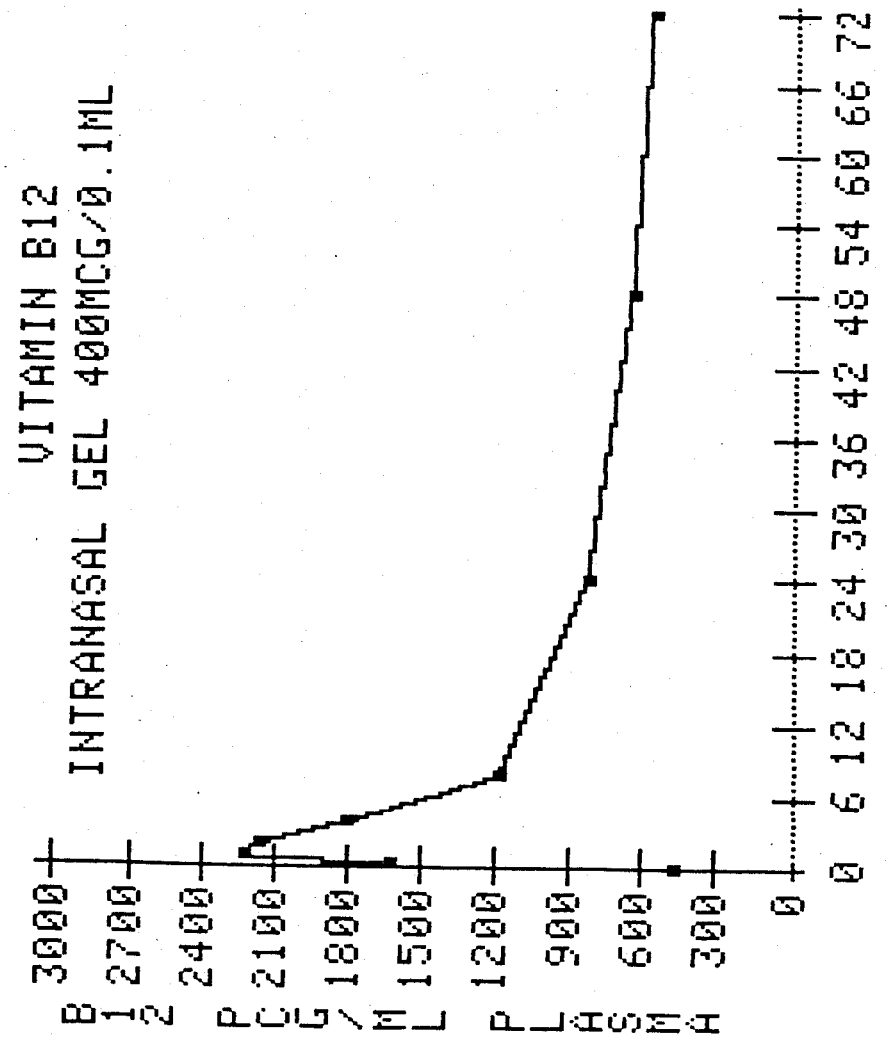

The results are shown in FIGS. 1, 2, 3 and 4 in which concentration in picograms per ml. is plotted against time. The results are also summarized in table 1. In the table, the baseline is the $B_{12}$ average concentration of $B_{12}$ in the volunteer group prior to $B_{12}$ administration.

From an analysis of the figures and the tables, the following unexpected advantages for nasal administration of $B_{12}$ in the compositions of this invention will be apparent:

1. Increased blood levels at lower dosages.
2. Maximum blood levels achieved more rapidly, and at lower dosage levels.
3. High blood levels maintained for entire period of test as indicated by larger areas under the carve.
4. Substantially higher blood levels at lower dosages even two days after administration.

TABLE 1
A COMPARISON OF THE BIOAVAILABILITY OF VITAMIN $B_{12}$ FOLLOWING INTRANASAL, ORAL, AND SUBLINGUAL ADMINISTRATION IN NORMAL SUBJECTS

| Number of Subjects | Vitamin $B_{12}$ Treatment | Average Baseline pc/ml | Average Maximum Increase in Plasma $B_{12}$ Concentration | Average time to Reach Maximum $B_{12}$ Plasma Concentration | Average Area Under The Curve (pcg hr/ml) | Average Increase In Plasma $B_{12}$ Concentration in 48 hrs. (pcg/ml) |
|---|---|---|---|---|---|---|
| 10 | 500 mcg Oral Tablet | 665.8 | 233.51 pcg/ml | 25.60 Hours | 9,503 | 92.6 |
| 10 | 500 mcg Sublingual Tablet | 599.8 | 196.64 pcg/ml | 5.70 Hours | 6,010 | 51.1 |
| 10 | 250 mcg Intranasal | 577.2 | 1167.31 pcg/ml | 2.5 Hours | 24,266 | 193.5 |
| 10 | 400 mcg | 472.1 | 1967.98 pcg/ml | 1.61 Hours* | 28,690 | 178.9 |

*A 24:00 hour data point was considered and outlier and eliminated from the calculation of the average.

What is claimed is:

1. A therapeutic composition for nasal administration comprising a therapeutically effective amount of a vitamin $B_{12}$, a pharmaceutically acceptable isotonic aqueous buffer to provide a pH of from about 4 to 6 and sufficient pharmaceutically acceptable thickening agent so that the viscosity of the composition is from about 2500 to 10,000 cps.

2. A therapeutic composition of claim 1 wherein the vitamin $B_{12}$ is cyanocobalamin.

3. A composition as in claim 1 or 2 additionally containing from about 1% to 10% by weight of a humectant.

4. A composition as in claim 1 or 2 additionally containing from about 0.2% to 2% by weight of a surfactant.

5. A composition as in claim 1 or 2 additionally containing from about 1% to 10% by weight of a humectant and from about 0.2% to 2% by weight of a surfactant.

6. A therapeutic composition as in claim 1 wherein the thickening agent is methyl cellulose.

7. A therapeutic composition of claim 6 wherein the vitamin $B_{12}$ is cyanocobalamin.

8. A therapeutic composition of claim 6 or 7 additionally containing from about 1% to 10% by weight of a humectant and from about 0.2% to 2% by weight of a surfactant.

9. A therapeutic composition for nasal administration in dosage unit form comprising from 50 to 1000 micrograms of a vitamin $B_{12}$, a pharmaceutically acceptable isotonic aqueous buffer to provide a pH of from about 4 to 6 and sufficient pharmaceutically acceptable thickening agent so that the viscosity of the composition is from about 2500 to 10,000 cps.

10. A therapeutic composition as in claim 9 wherein the vitamin $B_{12}$ is cyanocobalamin.

11. A therapeutic composition as in claim 9 or 10 additionally containing from about 1% to 10% by weight of a humectant.

12. A therapeutic composition as in claim 9 or 10 additionally containing from about 0.2% to 2% by weight of a surfactant.

13. A therapeutic composition as in claim 9 or 10 additionally containing from about 1% to 10% by weight of a surfactant.

14. A therapeutic composition as in claim 9 wherein the thickening agent is methyl cellulose.

15. A therapeutic composition as in claim 14 wherein the vitamin $B_{12}$ is a cyanocobalamin.

16. A therapeutic composition as in claim 14 or 15 additionally containing from about 1% to 10% by weight of a humectant and from about 0.2% to 2% by weight of a surfactant.

17. A method of treating a human for vitamin $B_{12}$ deficiency which comprises nasal administering to a human in need of such treatment a composition comprising a therapeutically effective amount of a vitamin $B_{12}$, a pharmaceutically acceptable isotonic aqueous buffer to provide a pH of from about 4 to 6 and sufficient pharmaceutically acceptable thickening agent so that the viscosity of the composition is from about 2500 to 10,000 cps.

18. A method as in claim 17 wherein the vitamin $B_{12}$ is cyanocobalamin.

19. A method as in claim 17 or 18 wherein the composition additionally contains from about 1% to 10% by weight of a humectant.

20. A method as in claim 17 or 18 wherein the composition additionally contains from about 0.2% to 2% by weight of a surfactant.

21. A method as in claim 17 or 18 wherein the composition additionally contains from about 1% to 10% by weight of a humectant and from about 0.2% to 2% by weight of a surfactant.

22. A method as in claim 17 wherein the thickening agent is methyl cellulose.

23. A method as in claim 22 wherein the vitamin $B_{12}$ is cyanocobalamin.

24. A method as in claim 22 or 23 wherein the composition additionally contains from about 1% to 10% by weight of a humectant and from about 0.2% to 2% by weight of a surfactant.

25. A composition as in claim 1 wherein the viscosity is from 2500 to 6500 cps.

26. A composition as in claim 9 wherein the viscosity is from 2500 to 6500 cps.

27. A method as in claim 17 wherein the viscosity of the composition is from 2500 to 6500 cps.

* * * * *